United States Patent [19]
Pylant

[11] Patent Number: 5,860,916
[45] Date of Patent: Jan. 19, 1999

[54] DISSOLVABLE TIP FOR A COLON HYDROTHERAPY SPECULUM SYSTEM AND METHOD OF MANUFACTURE AND USE THEREOF

[76] Inventor: Gary Lee Pylant, 12448 N. 9th Ave., Phoenix, Ariz. 85029

[21] Appl. No.: 637,297

[22] Filed: Apr. 24, 1996

[51] Int. Cl.⁶ .................................................. A61B 11/02
[52] U.S. Cl. .......................... 600/208; 600/235; 600/114; 604/275; 604/288
[58] Field of Search .................................. 600/201, 210, 600/206, 213, 208, 235, 114; 604/27, 41, 54, 56, 104, 170, 215, 239, 264, 265, 285, 286, 287, 288, 275

[56] References Cited

U.S. PATENT DOCUMENTS

| | | | |
|---|---|---|---|
| D. 282,204 | 1/1986 | Holt | D24/18 |
| 2,691,373 | 10/1954 | Bried | 604/275 |
| 2,863,454 | 12/1958 | Davidson et al. | 604/288 |
| 3,720,203 | 3/1973 | Brown | 128/4 |
| 3,762,410 | 10/1973 | Bindel | 128/229 |
| 3,881,485 | 5/1975 | Davis, Jr. | 128/270 |
| 4,190,059 | 2/1980 | Holt | 128/750 |
| 4,403,982 | 9/1983 | Clayton | 604/28 |
| 4,406,655 | 9/1983 | Clayton | 604/257 |
| 4,626,239 | 12/1986 | Ardizzone | 604/31 |
| 4,712,536 | 12/1987 | Hawks | 128/3 |
| 4,792,332 | 12/1988 | Lansel | 604/276 |
| 4,842,580 | 6/1989 | Ouelette | 604/30 |
| 4,842,583 | 6/1989 | Majlessi | 604/43 |
| 4,874,363 | 10/1989 | Abell | 604/28 |
| 4,943,285 | 7/1990 | Hawks | 604/275 |
| 5,019,056 | 5/1991 | Lee et al. | 604/257 |
| 5,049,138 | 9/1991 | Chevalier | 604/265 |
| 5,085,650 | 2/1992 | Giglio | 604/288 |
| 5,176,630 | 1/1993 | Shilling et al. | 604/41 |
| 5,250,024 | 10/1993 | Kensey | 604/275 |
| 5,279,542 | 1/1994 | Wilk | 604/19 |
| 5,281,212 | 1/1994 | Savage et al. | 604/265 X |
| 5,351,674 | 10/1994 | Hawks | 128/3 |
| 5,405,319 | 4/1995 | Abell et al. | 604/27 |

*Primary Examiner*—Beverly M. Flanagan
*Attorney, Agent, or Firm*—Steven Lin

[57] ABSTRACT

A dissolvable tip 20 or 40 for a colon hydrotherapy speculum system 100 that replaces the function of an obturator. The dissolvable tip 20 or 40 is made of a body of dissolvable material wherein a surface of the tip 20 or 40 is inserted and snugly fit into an inserting end 17 of a speculum 10 while another surface of the tip 20 or 40 with the speculum 10 is inserted into the anal, rectal, or colon canal 91 of a patient 90. The dissolvable tip 20 or 40 is held at the inserting end 17 of the speculum 10. One embodiment of the present invention discloses the dissolvable tip 20 as a pill shaped and egg shaped tip. Another embodiment of the present invention discloses the dissolvable tip 40 as similar in shape to dissolvable tip 20, but the dissolvable tip 40 further has a circumferential bulge 44 in its body wherein the circumferential bulge 44 has an edge that contacts the perimeter of the inserting end 17 of speculum 10 to allow a further snug attachment between the dissolvable tip 40 and the speculum 10. The colon hydrotherapy machine 130 of system 100 allows inlet washing fluid to flow from the machine 130 through the hose 110 and speculum 10 and to the tip 20 or 40 so that the tip 20 or 40 dissolves into the patient and inlet washing fluid flows into a colon area of the patient that is to be cleaned. Outlet fluid is able to flow from the colon area, through outlet end 18 of speculum 10, and through outlet hose 120. The material used to make the dissolvable tip 20 or 40 can have the further properties or characteristics of a deodorizer or a disinfectant or can function as a laxative or a type of medicine that helps the colon or rectal area of a patient 90. Tips 20 and 40 can also be made to be a natural product (i.e. made of herbs and other such components) that can be easily dissolved within the patient without any serious risks or hazards to the patient.

19 Claims, 4 Drawing Sheets

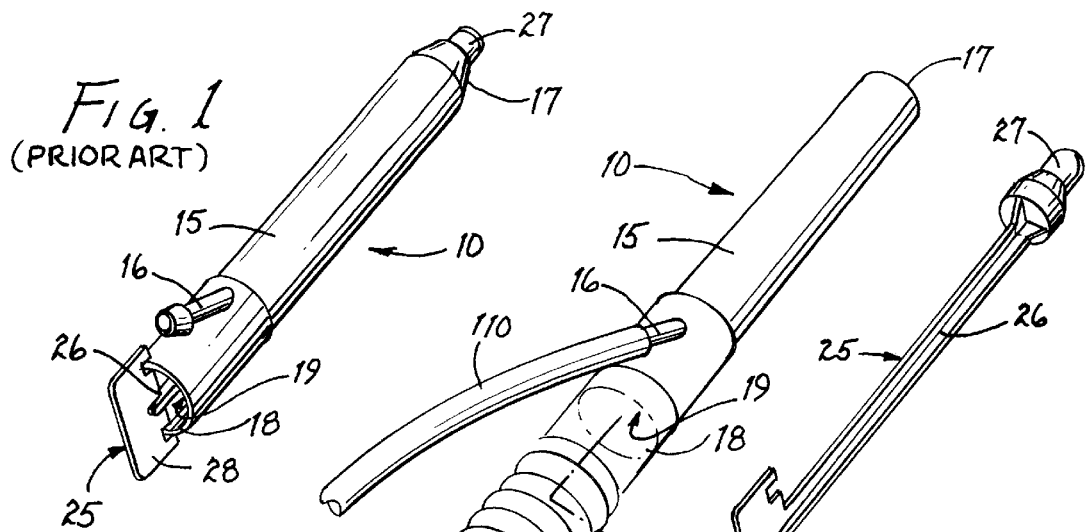
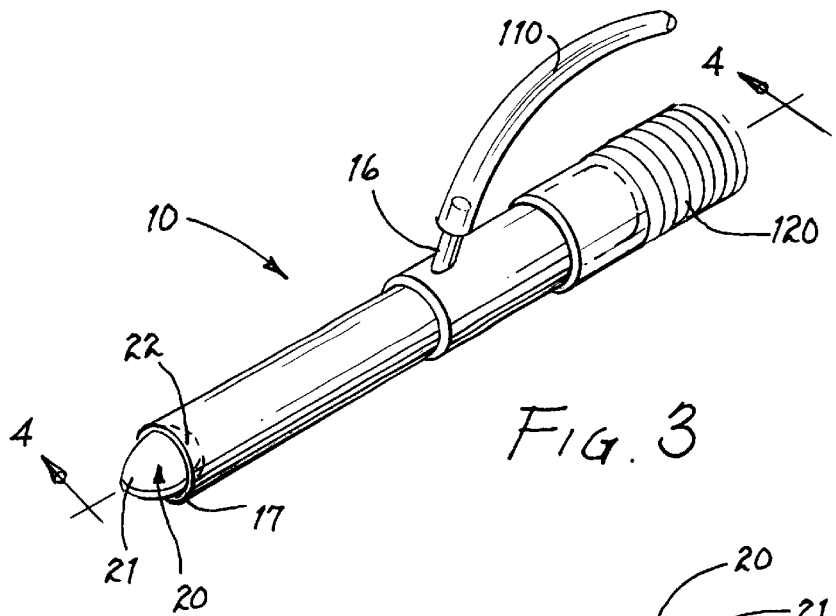
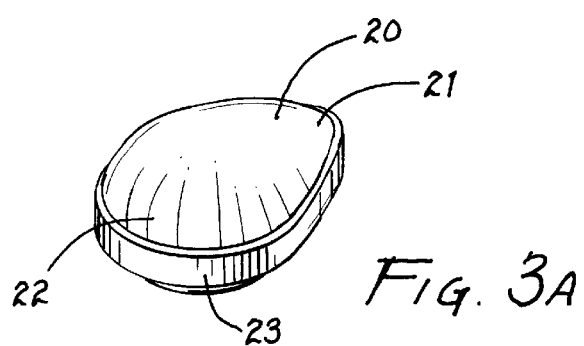

DISSOLVABLE TIP FOR A COLON HYDROTHERAPY SPECULUM SYSTEM AND METHOD OF MANUFACTURE AND USE THEREOF

BACKGROUND OF THE INVENTION

1. Fields of Invention

The present invention relates generally to a device used with a colon hydrotherapy speculum system, and, more particularly, relates to a dissolvable tip that is used with the speculum of a colon hydrotherapy system that provides colonic lavage.

2. Discussion Of Background And Prior Art

A number of people have difficulty with their bowel movements or do not have the ability to voluntarily evacuate their bowels (i.e. especially the elderly and the handicapped). Other people suffer from colitis or other related colon, rectal, or bowel ailments or diseases, which require ravaging or washing of the lower intestinal tract (i.e. the colon or rectal areas). In these cases, the people have to regularly use an enema, manually remove the fecal matter, or use a colonic irrigation or lavaging system.

The problems with colonic irrigation or lavaging systems are that the insertion of the nozzles or speculum of these devices can be very uncomfortable, unsanitary (i.e. including but not limited to fecal matter involuntarily excreting from the patient), and the lavage fluid motion produced by these systems may not be effective in loosening up and purging the fecal matter. In order to facilitate insertion of the speculum in the patient's rectal or anal canal and alleviate some of the discomfort, an obturator is used in conjunction with the speculum. FIGS. 1 and 2 show a prior art speculum 10 and an obturator 25. The speculum 10 has a main tubular portion 15 having a hollow interior 19, a small inlet tube 16 intersecting the main tubular portion 15 so that inlet fluids can be introduced into the speculum an inlet end 17, and an outlet end 18. The obturator 25 has an elongated rod 26, a rounded tapered end 27, and a small handle portion 28.

The obturator 25 is inserted through an end 18 of the speculum 10, through hollow interior 19 to extend through the end 17. The rounded tapered end 27 facilitates insertion of the speculum 10 into the patient's rectum or colon area (i.e. via the anal canal). After the speculum 10 is inserted, the obturator 25 is then removed from the speculum 10 by using the small handle portion 28. Other examples of typical rectal assembly for use with a colonic lavaging machine that include a speculum and an obturator are disclosed in U.S. Pat. No. 4,712,536 to Hawks and U.S. Pat. No. 4,874,363 to Abell.

One problem with the prior art speculum 10 and obturator 25 is that the concentric tube structure and the non-typical shaped obturator structure makes the speculum 10 and obturator 25 more difficult and expensive to manufacture (i.e. usually plastic which requires an injection molding process). Another main problem with the prior art speculum 10 and obturator 25 is that the inlet hose or conduit 110 is attached to the small inlet tube 16 and the outlet hose or conduit 120 is attached to the outlet end 18 after the speculum 10 is inserted and the obturator 25 is removed. The attachment of these hoses or conduits 110 and 120 can be painfill to the patient since the inserting end 17 of speculum 10 can move or slip within the patient's rectum or colon area when the hoses or conduits 110 and 120 are being attached.

A further problem is that after the obturator 25 is removed from the speculum 10 and before the hoses or conduits 110 and 120 are attached, the patient could involuntary excrete fecal matter through the openings and hollow of the speculum 10 (i.e. creating a mess and unsanitary situation). A still further problem that exists with obturators is that they are typically disposed after they are used one time. Since obturators are made of plastic, they can pose an environmental hazard or problem (i.e. they are not biodegradable).

Lubricants or jells have been used to aid the insertion of devices through the rectum or anal canal area. U.S. Pat. No. 3,881,485 to Davis, Jr. ("Davis") discloses a device for insertion through the anus into the upper rectum for the purpose of wiping the walls of the rectum clean of feces and stopping and retaining feces hi the colon and rectum at a distance from the anus. The invention is a preformed fiber device that is shaped for insertion through the anus into the upper rectum. The device is inserted through the anus and up through the rectum with a coating of non-irritating lubricant applied to the wiper plug. The lubricant should preferably be an organic, inert, water soluble jell, but other suitable lubricants may be used.

Other prior art patents disclose colon cleaning systems and methods that introduce enema solution (i.e. preferably with a laxative) into the colon through the anal opening via a suitable tube held in the rectum by an inflated bladder or balloon. The balloon and tube is secured to the patient (i.e. via the anus and to the rectum/colon). U.S. Pat. No. 4,403,982 to Clayton, U.S. Pat. No. 4,406,655 to Clayton, and U.S. Pat. No. 4,842,583 to Majlessi provide examples of such devices. However, these bladder or balloon devices require regulation of the pressure to the bladder or balloon, and they have the problem of the possibility of injury occurring to the patient if the pressure is not regulated properly.

A tip that dissolves in a person used in conjunction with a catheter appears to have been taught. U.S. Pat. No. 5,049,138 to Chevalier et al. ("Chevalier") discloses a catheter having such a dissolvable tip. The catheter includes a flexible tubular member that has an inner lumen and a rigid solid tip disposed at the end of the inner lumen. The tip (i.e. cone shaped) is formed of a material that is slippery when wet, soluble in the bodily fluids and capable of absorbing radiographic fluids that are injected into the inner lumen for identification of the location of X-rays. The solid tip is preferably formed of a water soluble polymer such as polyvinyl alcohol although alternatives are available such as polyethylene oxide, polyethylene glycol, polyacrylamides, polyvinyl pyrolidone, polyacrylic and the like. A narrow passageway is disposed in the tip and extends from the inner lumen to the distal end of the tip. The passageway is adapted to receive a guide wire for insertion of the catheter into an internal organ.

Presently, there does not exist in the prior art or on the market a dissolvable tip that is used in aiding the insertion of a speculum into the anus or rectum/colon area of a patient which is used in conjunction with a colon hydrotherapy speculum system. Therefore, an apparatus and method that is cost effective, environmentally safe and produces no waste hazard or problems, and would allow easy and less painful inserting of a speculum into the rectum or colon area of a person or animal are needed and desired. Also, a dissolvable tip for a colon hydrotherapy speculum system that is used and dissolved entirely within the colon and rectal area of the patient presently does not exist. Furthermore, an apparatus and method of inserting a speculum into the rectum or colon area of a person that is more sanitary (i.e. prevents fecal matter from involuntary excreting when the speculum is inserted) and further helps loosen or break up fecal matter in the colon or rectal area prior to lavaging or washing are also needed and desired.

Additionally, a dissolvable tip for a colon hydrotherapy speculum system that comprises dissolvable material that can deodorize, disinfect, functions as a laxative, or function as a medicine also does not exist. It is an object of the present invention to overcome the problems and limitations of the prior art that have been discussed. It is also another object of the present invention to be able to apply the principles and advantages of this invention to other related applications (i.e. including but not limited to animals).

SUMMARY OF THE INVENTION

Set forth is a brief summary of the invention in order to solve the foregoing problems and achieve the foregoing and other objects, benefits, and advantages in accordance with the purposes of the present invention as embodied and broadly described herein.

Accordingly, it is an object and advantage of the present invention to provide a dissolvable tip for a speculum used in a colon hydrotherapy system that provides colonic lavage to a patient wherein the dissolvable tip is used with the speculum to aid insertion of the speculum into an anal canal of the patient wherein the dissolvable tip includes a body of dissolvable material which has at least one surface that can be received by an inserting end of the speculum and which also has at least one surface that can be inserted into the anal canal of the patient.

It is a further aspect and advantage of the present invention to provide a dissolvable tip for a speculum wherein the at least one surface that can be received by an inserting end of the speculum is a generally parabolic surface that is adapted to fit into an open circular end of the speculum and hold the dissolvable tip at this end of the speculum.

It is a further aspect and advantage of the present invention to provide a dissolvable tip for a speculum wherein the at least one surface that can be inserted into the anal canal of the patient is a generally parabolic surface.

It is another object and advantage of the present invention to provide a method of making a dissolvable tip for a speculum used in a colon hydrotherapy system that provides colonic lavage to a patient wherein the dissolvable tip is used with the speculum to aid insertion of the speculum into an anal canal of the patient wherein the method includes the steps of providing dissolvable material and forming the dissolvable material into a shape of a body wherein the body has at least one surface that can be received by an inserting end of the speculum and wherein the body further has at least one surface that can be inserted into the anal canal of the patient.

It is still another object and advantage of the present invention to provide a method of using a dissolvable tip in a colon hydrotherapy speculum system that provides colonic lavage to a patient including the steps of providing a colon hydrotherapy machine that controls washing fluid flow, providing at least one hose through which washing fluid can flow, attaching an end of the at least one hose to the colon hydrotherapy machine, providing a speculum that is adapted to be inserted into an anal canal of a patient, attaching another end of the at least one hose to the speculum, providing a dissolvable tip that has a body of dissolvable material wherein the body has at least one surface that can be received by an inserting end of the speculum and wherein the body further has at least one surface that can be inserted into the anal canal of the patient, securely fitting the at least one surface of the dissolvable tip that can be received by an inserting end of the speculum into the inserting end of the speculum inserting the dissolvable tip and the inserting end of the speculum into the anal canal of the patient, activating the colon hydrotherapy machine to allow inlet washing fluid to flow from the machine through the hose and speculum and to the tip so that the tip dissolves into the patient and inlet washing fluid flows into a colon area of the patient that is to be cleaned and outlet fluid flows from the colon area, and controlling the inlet washing fluid that flows to the colon area of the patient and the outlet fluid that flows from the colon area.

It is still another object and advantage of the present invention to provide a colon hydrotherapy speculum system that provides colonic lavage to a patient including a colon hydrotherapy machine that controls washing fluid flow, at least one hose through which washing fluid can flow wherein one end of the at least one hose is attached to the colon hydrotherapy machine, a speculum that is adapted to be inserted into an anal canal of a patient wherein another end of the at least one hose is attached to the speculum, and a dissolvable tip securely fitted into an inserting end of the speculum wherein the dissolvable tip and the inserting end of the speculum can be inserted into the anal canal of the patient and wherein the colon hydrotherapy machine allows inlet washing fluid to flow from the machine through the hose and speculum and to the tip so that the tip dissolves into the patient and inlet washing fluid flows into a colon area of the patient that is to be cleaned and outlet fluid flows from the colon area.

It is another object and advantage of the present invention to provide an apparatus and method that is cost effective, environmentally safe and produces no waste hazard or problems, and would allow easy and less painful inserting of a speculum into the rectum or colon area of a person or animal.

It is another object and advantage of the present invention to provide a dissolvable tip for a colon hydrotherapy speculum system that is used and dissolves entirely within the colon or rectal area of the patient.

It is another object and advantage of the present invention to provide an apparatus and method of inserting a speculum into the rectum or colon area of a person or animal that is more sanitary (i.e. prevents fecal matter from involuntary excreting when the speculum is inserted) and further helps loosen or break up fecal matter in the colon or rectal area prior to lavaging or washing.

It is another object and advantage of the present invention to provide a dissolvable tip for a colon hydrotherapy speculum system that comprises dissolvable material that can deodorize, disinfect, function as a laxative, or functions as a medicine.

BRIEF DESCRIPTION OF THE DRAWINGS

FIG. 1—Perspective view of prior art speculum and obturator showing the obturator inserted into the speculum FIG. 2—Perspective view of prior art speculum and obturator showing the speculum and obturator separately and showing hoses or conduits attached to the speculum.

FIG. 3—Perspective view of the preferred embodiment dissolvable tip inserted into a speculum that has hoses or conduits attached to it.

FIG. 3A—Perspective view of the preferred embodiment dissolvable tip for a colon hydrotherapy speculum system.

DETAILED DESCRIPTION OF THE PREFERRED EMBODIMENT

Figure 4:
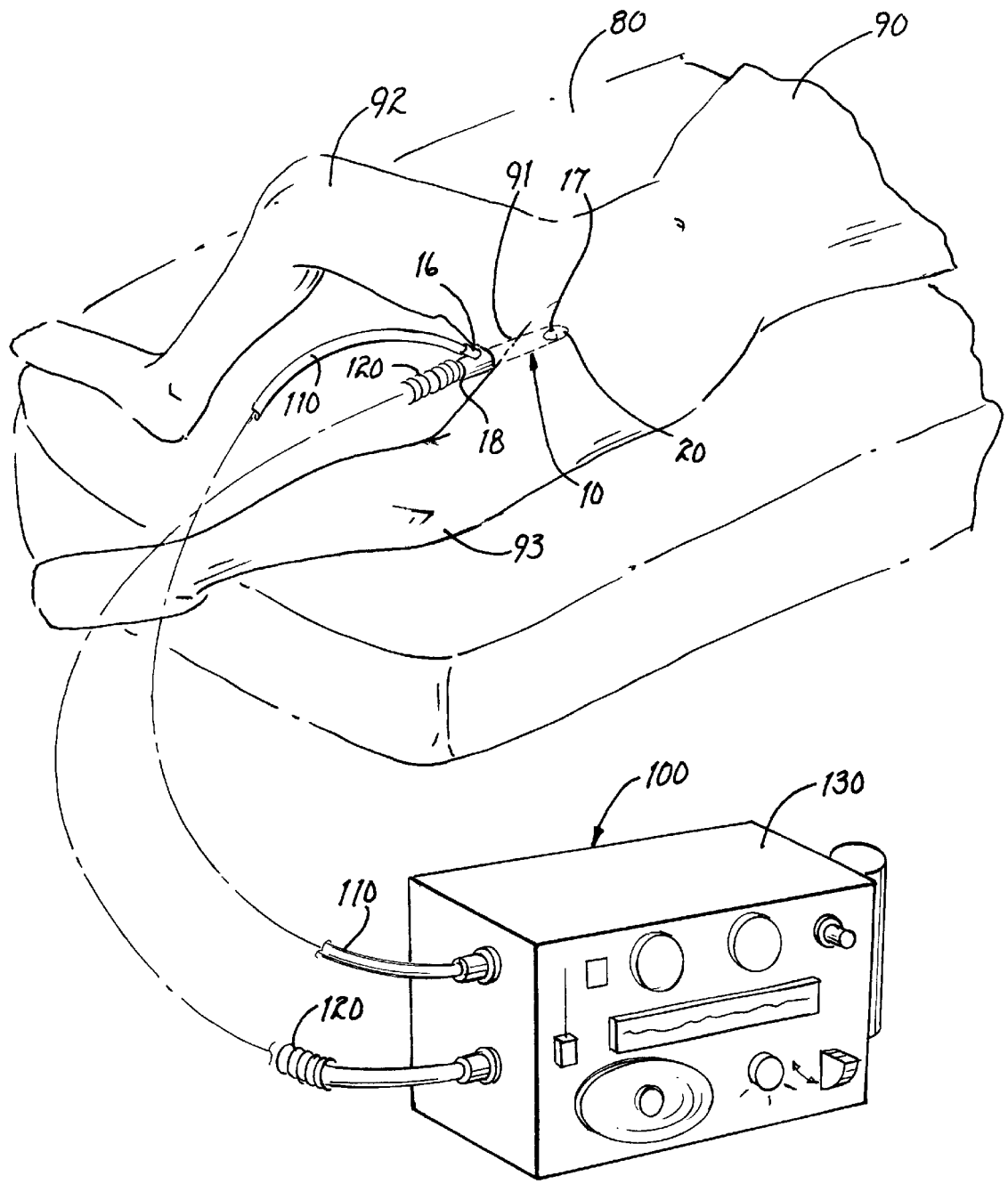
FIG. 4—Perspective view of a colon hydrotherapy speculum system utilizing the preferred embodiment dissolvable tip shown inserted with the speculum into a patient who is generally lying on a surface.
Figure 5:
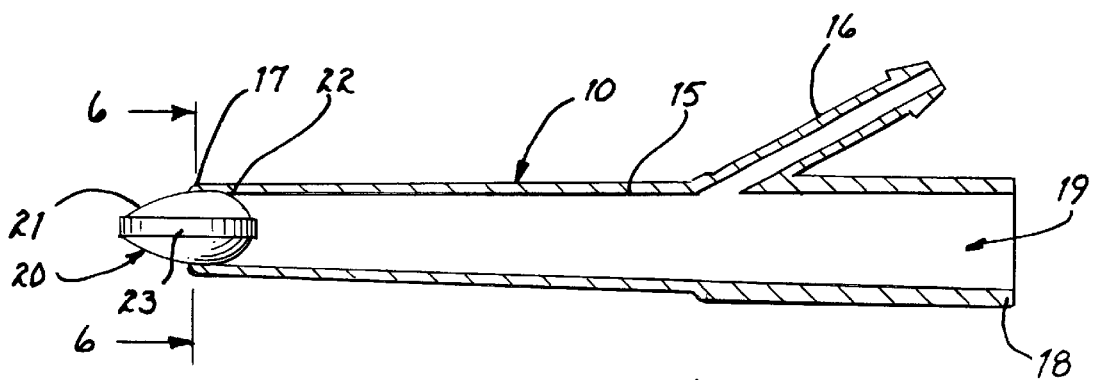
FIG. 5—Side view of the preferred embodiment dissolvable tip inserted into a speculum.

FIGS. 1 and 2 show a prior art speculum 10 and an obturator 25. The speculum 10 and obturator 25 are inserted into a patient's rectal or canal area. As stated earlier in the prior art and background section, inlet hose or conduit 110 is attached to the small inlet tube 16 and the outlet hose or conduit 120 is attached to the outlet end 18 after the speculum 10 is inserted and the obturator 25 is removed. The attachment of these hoses or conduits 110 and 120 can be painful to the patient since the inlet end 17 of speculum 10 can move or slip within the patient's rectum or colon area when the hoses or conduits 110 and 120 are being attached. A further problem is that after the obturator 25 is removed from the speculum 10 and before the hoses or conduits 110 and 120 are attached, the patient could involuntary excrete fecal matter through the openings and hollow of the speculum 10 (i.e. creating a mess and unsanitary situation). Furthermore, the speculum 10 and obturator 25 are generally made of hard plastic, and they typically are disposed after they have been used one time. The hard plastic, however, poses environmental issues or hazards when the speculum 10 and the obturator 25 are disposed.

Figure 6:
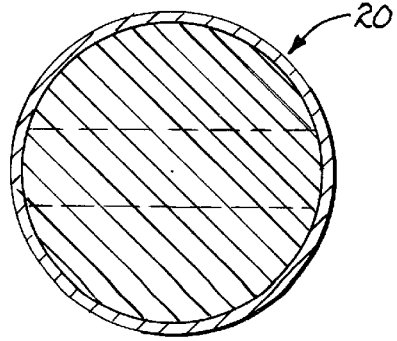
FIG. 6—Cross-sectional view of the preferred embodiment dissolvable tip according to the line 6—6 of FIG. 5.
Figure 8:
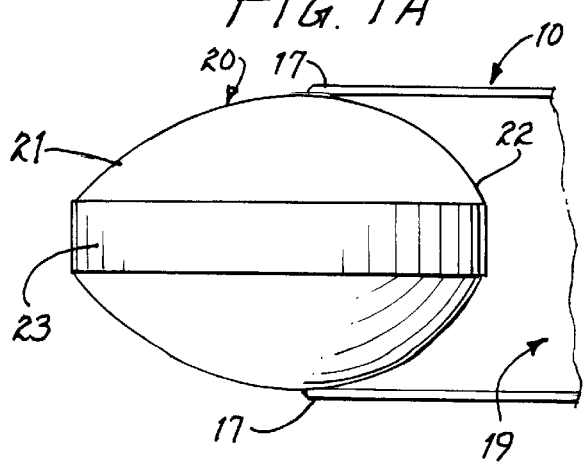
FIG. 8—Side view of the preferred embodiment dissolvable tip inserted into an inserting end of the speculum.

The present invention has been developed to replace obturators and to overcome their problems and disadvantages. FIGS. 3 and 3A show the first preferred embodiment dissolvable tip 20. FIGS. 3, 3A, 5, 7, 7A, and 8 show the first preferred embodiment dissolvable tip 20 having a surface 21 and surface 22. Surfaces 21 and 22 are generally parabolic, curved surfaces. Surface 21 is shown to be a generally narrower parabolic surface while surface 22 is a generally wider parabolic surface. Furthermore, FIG. 6 shows a cross-sectional view of the first preferred embodiment dissolvable tip 20 (i.e. shows the tip having a circular cross section).

In FIGS. 3, 5, 7A, and 8, surface 22 is shown to be preferably inserted and received by an inserting end 17 of the speculum 10. The surface 22 of tip 20 is snugly fitted into the open circular (i.e. inserting) end 17 of the speculum 10, and the dissolvable tip 20 is held at the end 17. In FIGS. 3, 5, 7A, and 8, surface 21 and inserting end 17 of speculum 10 can be inserted into the anal canal 91 of patient 90 (i.e. see FIG. 4).

Figures 7, 7A:
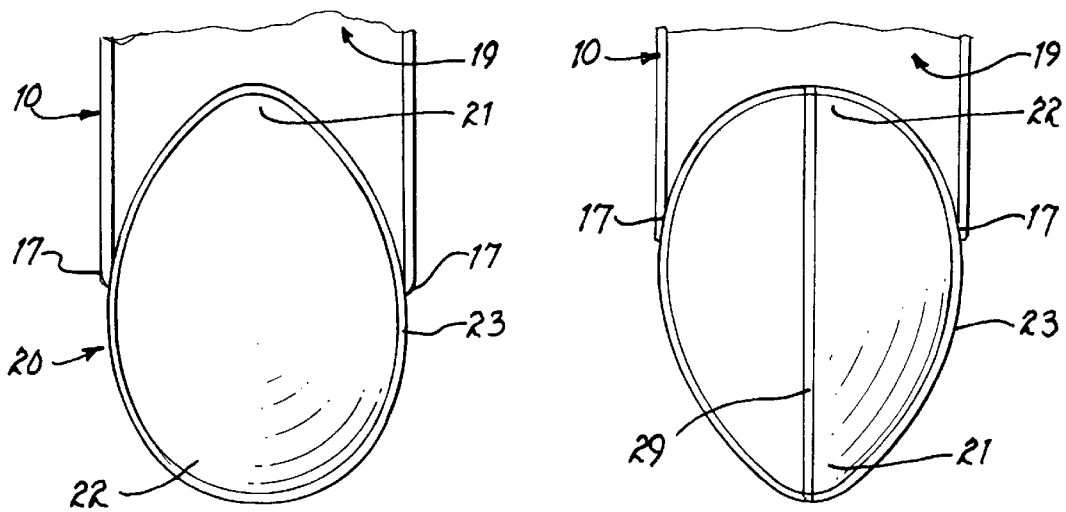
FIG. 7—Top view of the preferred embodiment dissolvable tip inserted into a speculum wherein the narrower parabolic surface is shown inserted into the interior of the speculum.
FIG. 7A—Top view of the preferred embodiment dissolvable tip inserted into a speculum wherein the wider parabolic surface is shown inserted into the interior of the speculum.

Alternatively, as shown in FIG. 7, surface 21 can be inserted and received by an inserting end 17 of speculum 10.

In this case, the surface 21 of tip 20 is snugly fitted into the open circular (i.e. inserting) end 17 of the speculum 10, and the dissolvable tip 20 is held at the end 17. Surface 22 and inserting end 17 of speculum 10 are then inserted into the anal canal 91 of patient 90.

Figure 9:
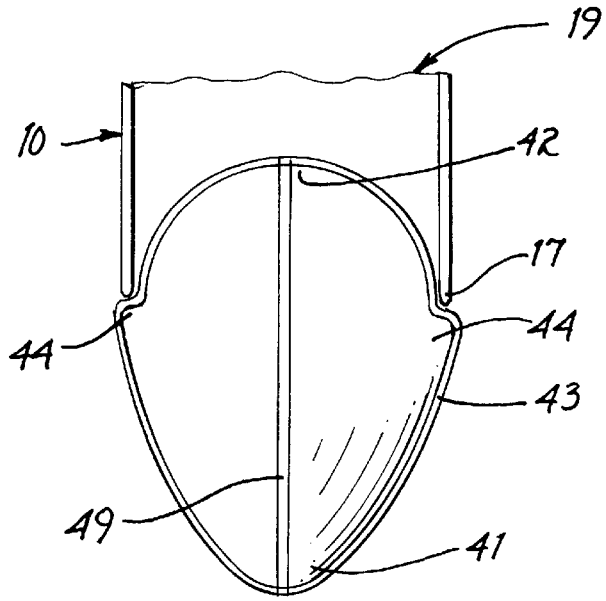
FIG. 9—Top view of a second embodiment dissolvable tip having a bulge in the body wherein the wider parabolic surface is shown inserted into the interior of the speculum.
Figure 10:
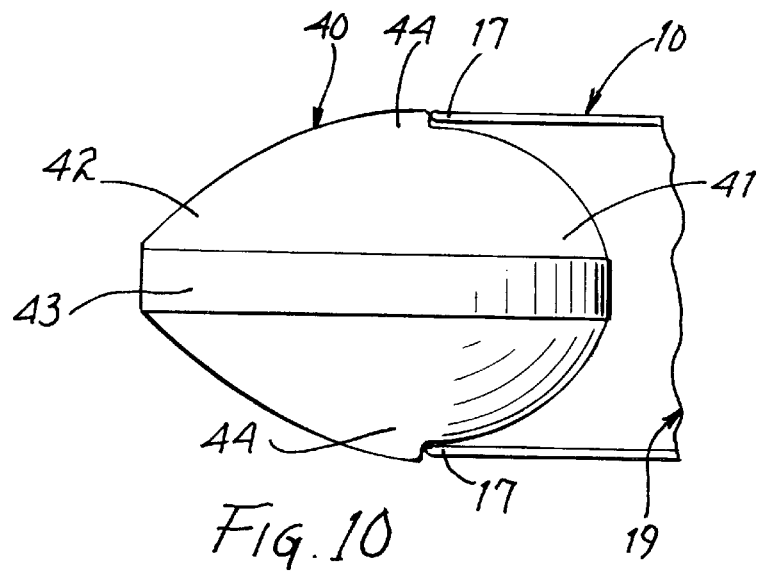
FIG. 10—Side view of the second embodiment dissolvable tip inserted into an inserting end of the speculum.
Figure 11:
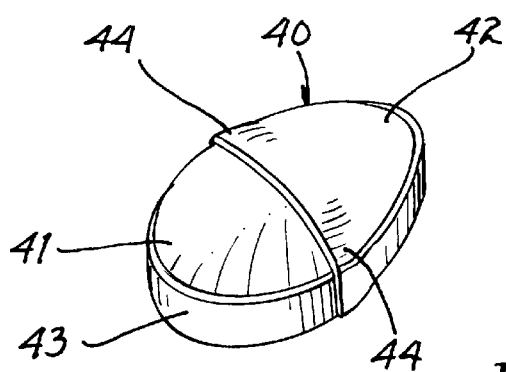
FIG. 11—Perspective view of the second embodiment dissolvable tip for a colon hydrotherapy speculum system.

As shown in FIGS. 3, 3A, 4, 5, 7, 7A, and 8, the tip 20 is in the general shape of a pill (i.e. general ovular shape, general egg shape, or other such shapes). The tip 20 can take the form of an ovular shape (i.e. not shown) or egg shape (i.e. as shown in the figures). FIGS. 9, 10, and 11 show an alternative embodiment dissolvable tip 40. Tip 40 also has a generally narrower parabolic surface 41 and a generally wider parabolic surface 42. Tip 40 is similar to tip 20 (i.e. egg shaped). However, tip 40 further has a circumferential bulge 44 around the main body of the tip 40. In this embodiment, wider surface 42 of tip 40 is preferably inserted into the end 17 of speculum 10 and into the hollow interior 19 of speculum 10. Tip 40 is fitted into the open circular (i.e. inserting) end 17 of the speculum 10 so that the edge of the circumferential bulge 44 contacts the perimeter of the inserting end 17 to allow a further snug attachment between the dissolvable tip 40 and the speculum 10. The dissolvable tip 40 is held at the inserting end 17.

The tip 20 or 40 is made from a body of dissolvable material. The body of dissolvable material has at least one surface (i.e. surface 22 shown in FIG. 7A or surface 21 shown in FIG. 7 or surface 42 in FIG. 9) that can be received by an inserting end 17 of the speculum 10, and it also has at least one surface (i.e. surface 21 shown in FIG. 7A or surface 22 shown in FIG. 7 or surface 41 in FIG. 9) that can be inserted into the anal canal of the patient 90. The tip 20 or 40 is generally made by providing dissolvable material and forming the dissolvable material into a shape of a body wherein the body has at least one surface that can be received by an inserting end 17 of the speculum 10 and has at least one surface that can be inserted into the anal canal.

Some of the dissolvable material provided for making the tip 20 or 40 includes combining a dry powder mixture of alfalfa, calcium sulfate, modified cellulose gum, polyplasdone XL, and magnesium stearate. The dry powder mixture can further include mint and aloe vera. The tip 20 or 40 are made by placing the dry powder mixture of alfalfa, calcium sulfate, modified cellulose gum, polyplasdone XL, magnesium stearate, mint, and aloe vera into a mold that forms a desired shape of the dissolvable tip (i.e. pill shaped and egg shaped which is shown in perspective in FIG. 3A, or ovular pill shaped which is not shown, or pill shaped and egg shaped with a circumferential bulge 44 as shown in perspective in FIG. 11). The dry powder mixture is then compressed in the mold so that the desired shape of the dissolvable tip is formed. The present invention is not limited to these components, compounds, or materials, and other such suitable or equivalent mixtures may be also used to make the tip 20 or 40. Furthermore, any type of suitable dissolvable material can generally be used to make the dissolvable tip 20 or 40. If other suitable or equivalent dissolvable materials are used to make the tip 20 or 40, then these dissolvable materials would be formed into the same way by placing the dissolvable material into a mold that forms a desired shape and the material is then compressed into the desired shape of the dissolvable tip (i.e. including but not limited to the shapes of tips 20 and 40).

The material used to make the dissolvable tip 20 or 40 can further have the properties or characteristics of a deodorizer or a disinfectant or can function as a laxative or a type of medicine that helps the colon or rectal area of a patient 90. Tips 20 and 40 can also be made to be a natural product (i.e.

made of herbs and other such components) that can be easily dissolved within the patient without any serious risks or hazards to the patient. A natural product dissolvable tip 20 or 40, which is not considered a medicine or drug, would have the further advantage of not being an environmental hazard and would not pose any serious waste disposal issues, and the natural product tip 20 or 40 may not have to be highly scrutinized by the Food and Drug Administration (FDA) since the tip 20 or 40 may not be classified as a drug or medicine.

As shown in FIGS. 7A and 9, tips 20 and 40 respectively have a groove 29 and a groove 49. The grooves 29 and 49 are located lengthwise along the body of the dissolvable tips 20 and 40, and these grooves span all the way around the entire lengthwise body leaving channels or openings between the inserting end 17 of speculum 10 and the tip 20 or 40 through which washing fluid can flow. The grooves 29 and 49 allow washing fluid to flow through and out of the speculum 10 to the anal, rectal, or colon area(s) of the patient. These grooves 29 and 49 prevent the build up of washing fluid and swelling at the tips 20 or 40 when washing fluid is allowed to flow through the speculum 10, and they help ensure that the tips 20 and 40 dissolve.

Referring to FIG. 4, the dissolvable tip 20 or 40 is used in a colon hydrotherapy speculum system 100. In FIG. 4, the patient 90 is shown lying on a flat surface 80 on his/her back. The legs 92 and 93 of patient 90 are generally spread apart. The colon hydrotherapy speculum system 100 includes the main components of the typical or conventional colon lavaging or washing system. The colon hydrotherapy system 100 includes a colon hydrotherapy machine 130 that is attached to a source of washing fluid and can control the flow of washing fluid to and from the machine 130. An end of an inlet hose 110 and an end of an outlet hose 120 are attached to the machine 130. The other end of the inlet hose 110 is attached to the small inlet tube 16 intersecting the main tubular portion 15 of speculum 10, and the other end of the outlet hose 120 is attached to the outlet end 18 of speculum 10.

At least one surface of the dissolvable tip 20 or 40 is inserted and snugly fitted into the inserting end 17 of speculum 10 (i.e. as described earlier in this description). As shown in FIG. 4, the dissolvable tip 20 or 40 with speculum 10 having the already attached hoses 110 and 120 are inserted between the legs 92 and 93 of patient 90 and through the anal or rectal canal area 91. The dissolvable tip 20 or 40 with speculum 10 are inserted with the hoses 110 and 120 already attached which prevents further discomfort to the patient (i.e. hoses do not have to be attached after speculum 10 is inserted into the anal or rectal area). Furthermore, tip 20 or 40 prevents fecal matter from involuntarily being excreted from the patient into the speculum 10 after it is inserted into the anal, rectal, or colon area. The colon hydrotherapy machine 130 is activated to allow inlet washing fluid to flow from the machine 130 through the hose 110 and speculum 10 and then to the dissolvable tip 20 or 40. The tip 20 or 40 is dissolved by the washing fluid and into the patient 90. The inlet washing fluid flows into a colon or rectal area of the patient 90 that is to be cleaned.

As stated earlier, the dissolved tip 20 or 40 can be made of material that have properties or characteristics of a deodorizer or a disinfectant or can function as a laxative or a type of medicine that helps the colon or rectal area of a patient 90. Therefore, the tip 20 or 40, after being dissolved into the patient 90, can provide these further functions or any other types of suitable functions. Furthermore, after the washing fluid is filled into the colon or rectal area of the patient 90, then machine 130 controls the outflow of the washing fluid (i.e. outlet washing fluid) from the colon or rectal area and through the outlet end 18 of speculum 10 and through the outlet hose 120.

Therefore, the present invention dissolvable tip 20 or 40 provides an apparatus and method that replaces the function of an obturator, and it is also cost effective, environmentally safe, produces no waste hazard or problems, and would allow easy and less painful inserting of a speculum into the rectum or colon area of a person. The dissolvable tip 20 or 40 for a colon hydrotherapy speculum system 100 has the advantages of being used and dissolved entirely within the colon and rectal area of the patient, which reduces the environmental or waste issues that may be raised. Furthermore, the present invention provides an apparatus and method of inserting a speculum into the rectum or colon area of a person that is more sanitary (i.e. prevents fecal matter from involuntary excreting when the speculum is inserted) and further helps loosen or break up fecal matter in the colon or rectal area prior to lavaging or washing (i.e. since the dissolvable materials used to make the dissolvable tip 20 or 40 could also have the functions of a laxative or medicine).

As stated earlier, a dissolvable tip 20 or 40 for a colon hydrotherapy speculum system 100 that comprises dissolvable material that can deodorize, disinfect, function as a laxative, or functions as a medicine has been disclosed by the present invention. Tips 20 and 40 have the further advantage of being able to be made as a natural product (i.e. made of herbs and other such components) that can be easily dissolved within the patient 90 without any serious risk or hazard to the patient 90. A natural product dissolvable tip 20 or 40 that is not considered a drug or medicine has the further advantage of not being an environmental hazard and would not pose a large waste disposal issue. The natural product classification of this tip 20 or 40 could avoid the high standard scrutiny for drugs and medicines that are set by the Food and Drug Administration (FDA). Furthermore, the principles and advantages of the present invention can be applied to not only persons but animals as well and could also be applied to any other related applications.

The foregoing description of a preferred embodiment and best mode of the invention known to applicant at the time of filing the application has been presented for the purposes of illustration and description. It is not intended to be exhaustive or to limit the invention to the precise form disclosed, and obviously many modifications and variations are possible in the light of the above teaching. The embodiment was chosen and described in order to best explain the principles of the invention and its practical application to thereby enable other skilled in the art to best utilize the invention in various embodiments and with various modifications as are suited to the particular use contemplated.

What is claimed is:

1. A dissolvable tip for a speculum used in a colon hydrotherapy system that provides colonic lavage to a patient wherein the dissolvable tip is used with the speculum to aid insertion of the speculum into an anal canal of the patient comprising:

a body of dissolvable material wherein the body has at least one generally parabolic surface that can be received by an inserting end of the speculum and that is adapted to fit into an open circular end of the speculum and hold the dissolvable tip at the end of the speculum and wherein the body further has at least one surface that can be inserted into the anal canal of the patient.

2. The dissolvable tip for a speculum according to claim 1 wherein:
the at least one surface that can be inserted into the anal canal of the patient is a generally parabolic surface.

3. The dissolvable tip for a speculum according to claim 1 wherein:
the body of dissolvable material is formed into a general ovular shape of a pill.

4. The dissolvable tip for a speculum according to claim 3 wherein the general ovular shape of the body of dissolvable material further comprises:
a circumferential bulge in the body of the dissolvable tip wherein the bulge has an edge that contacts a perimeter of the inserting end of the speculum to allow a snug attachment between the dissolvable tip and the speculum.

5. The dissolvable tip for a speculum according to claim 1 wherein:
the body of dissolvable material is formed into a general egg shape of a pill.

6. The dissolvable tip for a speculum according to claim 5 wherein the general egg shape of the body of dissolvable material further comprises:
a circumferential bulge in the body of the dissolvable tip wherein the bulge has an edge that contacts a perimeter of the inserting end of the speculum to allow a snug attachment between the dissolvable tip and the speculum.

7. The dissolvable tip for a speculum according to claim 1 wherein the dissolvable material used for making the body of the dissolvable tip comprises a dry powder mixture of alfalfa, calcium sulfate, modified cellulose gum, polyplasdone XL, and magnesium stearate.

8. The dissolvable tip for a speculum according to claim 7 wherein the mixture for making the body of the dissolvable tip further comprises mint and aloe vera.

9. The dissolvable tip for a speculum according to claim 1 further comprising:
a groove in the body of dissolvable material for allowing washing fluid to flow out of the speculum and for accelerating dissolution of the body.

10. A dissolvable tip for a speculum used in a colon hydrotherapy system that provides colonic lavage to a patient wherein the dissolvable tip is used with the speculum to aid insertion of the speculum into an anal canal of the patient comprising:
a body of dissolvable material formed into a general ovular shape of a pill wherein the body has at least one surface that can be received by an inserting end of the speculum and wherein the body further has at least one surface that can be inserted into the anal canal of the patient.

11. The dissolvable tip for a speculum according to claim 10 wherein the general ovular shape of the body of dissolvable material further comprises:
a circumferential bulge in the body of the dissolvable tip wherein the bulge has an edge that contacts a perimeter of the inserting end of the speculum to allow a snug attachment between the dissolvable tip and the speculum.

12. The dissolvable tip for a speculum according to claim 10 wherein the dissolvable material used for making the body of the dissolvable tip comprises a dry powder mixture of alfalfa, calcium sulfate, modified cellulose gum, polyplasdone XL, and magnesium stearate.

13. The dissolvable tip for a speculum according to claim 12 wherein the mixture for making the body of the dissolvable tip further comprises mint and aloe vera.

14. The dissolvable tip for a speculum according to claim 10 further comprising:
a groove in the body of dissolvable material for allowing washing fluid to flow out of the speculum and for accelerating dissolution of the body.

15. A dissolvable tip for a speculum used in a colon hydrotherapy system that provides colonic lavage to a patient wherein the dissolvable tip is used with the speculum to aid insertion of the speculum into an anal canal of the patient comprising:
a body of dissolvable material formed into a general egg shape of a pill wherein the body has at least one surface that can be received by an inserting end of the speculum and wherein the body further has at least one surface that can be inserted into the anal canal of the patient.

16. The dissolvable tip for a speculum according to claim 15 wherein the general egg shape of the body of dissolvable material further comprises:
a circumferential bulge in the body of the dissolvable tip wherein the bulge has an edge that contacts a perimeter of the inserting end of the speculum to allow a snug attachment between the dissolvable tip and the speculum.

17. The dissolvable tip for a speculum according to claim 15 wherein the dissolvable material used for making the body of the dissolvable tip comprises a dry powder mixture of alfalfa, calcium sulfate, modified cellulose gum, polyplasdone XL, and magnesium stearate.

18. The dissolvable tip for a speculum according to claim 17 wherein the mixture for making the body of the dissolvable tip further comprises mint and aloe vera.

19. The dissolvable tip for a speculum according to claim 15 further comprising:
a groove in the body of dissolvable material for allowing washing fluid to flow out of the speculum and for accelerating dissolution of the body.

* * * * *